(12) United States Patent
Hillairet et al.

(10) Patent No.: US 8,420,756 B2
(45) Date of Patent: Apr. 16, 2013

(54) POLYMERISATION OF ETHYLENE AND ALPHA-OLEFINS WITH CATALYST SYSTEMS BASED ON BINAM DERIVED LIGANDS

(75) Inventors: Caroline Hillairet, Soignies (BE); Guillaume Michaud, Lille (FR); Sabine Sirol, Horrues (BE)

(73) Assignee: Total Petrochemicals Research Feluy, Seneffe (Feluy) (BE)

( * ) Notice: Subject to any disclaimer, the term of this patent is extended or adjusted under 35 U.S.C. 154(b) by 602 days.

(21) Appl. No.: 12/596,082

(22) PCT Filed: Apr. 8, 2008

(86) PCT No.: PCT/EP2008/054227
§ 371 (c)(1),
(2), (4) Date: Apr. 14, 2010

(87) PCT Pub. No.: WO2008/125548
PCT Pub. Date: Oct. 23, 2008

(65) Prior Publication Data
US 2010/0210799 A1    Aug. 19, 2010

(30) Foreign Application Priority Data

Apr. 17, 2007  (EP) .................................... 07106303

(51) Int. Cl.
C08F 4/64   (2006.01)
C08F 4/76   (2006.01)
C08F 4/52   (2006.01)

(52) U.S. Cl.
USPC ........... 526/172; 526/161; 526/160; 526/170; 526/348; 526/348.5; 526/351; 526/352; 556/51

(58) Field of Classification Search .................. 526/172, 526/161; 556/51
See application file for complete search history.

(56) References Cited

U.S. PATENT DOCUMENTS 7,842,829 B2 * 11/2010 Hillairet et al. ............... 556/138

FOREIGN PATENT DOCUMENTS

| EP | 1 982 975 A1 | * | 10/2008 |
| JP | 2007-106734 A | * | 4/2007 |
| WO | WO 03/004506 | | 1/2003 |
| WO | WO 2007/006737 | | 1/2007 |
| WO | WO 2008/125548 A1 | * | 10/2008 |

OTHER PUBLICATIONS

Cloke et al., J. Organomet. Chem. 1996, 506, 343-345.*
Rigert et al., Eur. J. Inorg. Chem., 2007, 1159-1168.*
O'Shaughnessy et al., Organometallics, 2002, 21, 4496-4504.*
Tonzetich et al., Polyhedron, 2006, 25, 469-476.*
Scarborough et al., Angew. Chem. Int. Ed. 2005, 44,5269-5272.*
Aikawa et al., Chem. Commun. 2005, 5799-5801.*
Vyskocil et al., J. Org. Chem. 1998, 63, 7727-7737.*
Riegert et al., J. Org. Chem. 2006, 71, 2514-2517.*
Pertici et al., J. Organomet. Chem. 1996, 515, 163-171.*
Jamieson et al., Organometallics 2000, 19, 925-930.*
Kettunen et al. Organometallics 2004, 23, 3800-3807.*
Westmoreland et al., Organometallics 2004, 23, 5066-5074.*
Watson et al. Organometallics 2006, 25, 4731-4733.*
O'Shaughnessy et al. Tetrahedron: Aysmmetry 2003, 14, 1979-1983.*
Riegert, David et al: "Neutral yttrium tris(amide) and ate complexes coordinated by an (R)-N,N'-diisopropyl-1,1''-binaptithyl-2,2'binaphthyl-2,2'diamido ligand as enantioselective catalysts fo intramolecular hydroamination. Eur. J. Inorg. Chem. 2007, 8, 1159-1168.
Scarborough, Christopher C. et al: "Pdll complexes possessing a seven-membered N-heterocyclic carbene ligand" Angewandte Chemie, International Edition, 44 (33), 5259-5272 2005.
Watson, Donald A. et al: "Zirconium bis (amido) catalysts for asymmetric intramolecular alkene hydroamination" Organometallics, 25(20), 4731-4733 2006.
Riegert, David et al: "Enantioselective Intramolecular hydroamination catalyzed by lanthanide ate complexes coordinated by n-substituted (r)-1,1''-binaphthyl-2,2'-diamido ligan J. Org. Chem., 2006, 71(6), 2514-2517.
Collin; Jacqueline et al: Lanthanide complexes coordinated by n-substituted (R)1,1'-binaphthyl-2,2'-diamido ligands in the catalysis of enantioselective intramolecular hydro Chemistry—A European Journal, 2005, 11(11), 3455-3462.
Jamieson, Jennifer Y. et al: "Synthesis of molybdenum imido alkylidene complexes containing n,n'-disubstituted 2,2'-bisamido-1,1'-binaphthyl ligands" Organometallics, 19(5), 925-930, 2000.
Vyskocil, Stepan et al: Synthesis of n-alkylated and n-arylated derivatives of 2-amino-2'-hydroxy-1,1'-binaphthyl (Nobin) and 2,2'-diamino-1,1'-binaphthyl and their applicati J. Org. Chem., 1998, 63(22), 7727-7737.
Koch, Russell W. et al: "Electrochemical reduction of di-schiff bases, synthesis of piperazines, indoloindoles, diazepines, and diazoncines" Journal of Organic Chemistry, 47(2 J. Org. Chem. 1982, 41(23), 4452-4459.
Kettunem M et al: "Chiral Zirconium Complexes with Bianiline-Based N4-Donor Ligands" Organometallics, ACS, Washington, DC, US, vol. 23, No. 16, Aug. 2, 2004, p. 3800-3807.
Cloke, F. Geoffrey N. et al: "Novel zirconium complexes derived from C2-symmetric diamide ligands; the X-ray crystal structure of " Journal of Organometallic Chemistry 506(1-2 ) , 343-345, 1996.

* cited by examiner

*Primary Examiner* — Rip A. Lee

(57) ABSTRACT

The present invention relates to the field of single site catalyst systems based on aromatic BINAM diamine ligands and suitable for oligomerising or polymerising ethylene and alpha-olefins.

11 Claims, No Drawings

POLYMERISATION OF ETHYLENE AND ALPHA-OLEFINS WITH CATALYST SYSTEMS BASED ON BINAM DERIVED LIGANDS

CROSS-REFERENCE TO RELATED APPLICATIONS

This application claims the benefit of PCT/EP2008/054227, filed Apr. 8, 2008, which claims priority from EP 07106303.6, filed Apr. 17, 2007.

The present invention relates to the field of single site catalyst systems based on aromatic diamine ligands and suitable for oligomerising or polymerising ethylene and alpha-olefins.

There exists a multitude of catalyst systems available for polymerising or oligomerising ethylene and alpha-olefins, but there is a growing need for finding new systems capable to tailor polymers with very specific properties. More and more post-metallocene catalyst components based on early or late transition metals from Groups 3 to 10 of the Periodic Table have recently been investigated such as for example those disclosed in Gibson and al. review (Gibson, V. C.; Spitzmesser, S. K., Chem. Rev. 2003, 103, p. 283). But there is still a need to improve either the specificities or the performances of these systems.

It is an aim of the present invention to provide a new catalyst components based on aromatic diamine ligands.

It is another aim of the present invention to provide active catalyst systems based on these catalyst components.

It is a further aim of the present invention to provide a process for polymerising or for oligomerising ethylene and alpha-olefins with these new catalyst systems.

It is also an aim of the present invention to provide linear polyethylenes or oligomers by polymerising ethylene with these new catalysts systems.

Accordingly, the present invention discloses a ligand of general formula I

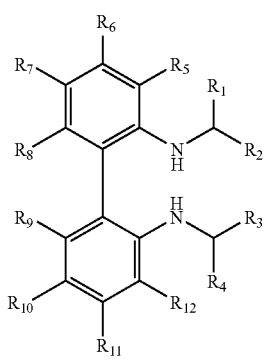

(I)

wherein $R_1$, $R_2$, $R_3$, $R_4$, $R_5$, $R_6$, $R_7$, $R_8$, $R_9$, $R_{10}$, $R_{11}$ and $R_{12}$ are each independently selected from hydrogen, unsubstituted or substituted hydrocarbyl, or inert functional group and two or more $R_1$'s can be linked together to form further ring or rings.

By inert functional group, is meant a group, other than hydrocarbyl or substituted hydrocarbyl, that is inert under the complexation conditions to which the compound containing said group is subjected. They can be selected for example from halo, ester, ether, amino, imino, nitro, cyano, carboxyl, phosphate, phosphonite, phosphine, phosphinite, thioether and amide. After metallation of the ligand, an inert functional group must not coordinate at all to the metal.

Preferably, $R_5$, $R_6$, $R_7$, $R_8$, $R_9$, $R_{10}$, $R_{11}$ and $R_{12}$ are each independently selected from hydrogen, unsubstituted or substituted alkyl groups, unsubstituted or substituted aryl groups, or unsubstituted or substituted cycloalkyl groups and if they are substituted, the substituents may be joined to form a closed structure. Most preferably, $R_5$, $R_6$, $R_{11}$ and $R_{12}$ are the same and they are hydrogen, and $R_7$ and $R_8$ together, as well as $R_9$ and $R_{10}$ together, are joined to form unsubstituted naphtyl groups.

Preferably, $R_1$, $R_2$, $R_3$ and $R_4$ are each independently selected from unsubstituted or substituted alkyl groups, unsubstituted or substituted aryl groups, or unsubstituted or substituted cycloalkyl groups and if they are substituted, the substituents may be joined to form a closed structure. More preferably, $R_1$, $R_2$, $R_3$ and $R_4$ are the same and are phenyls wherein Ph is phenyl unsubstituted or substituted or wherein $R_1$ and $R_2$ on one hand and $R_3$ and $R_4$ on the other hand are linked together and form fluorenyl groups unsubstituted or substituted, When $R_1$, $R_2$, $R_3$ and $R_4$ are substituted the substituents may advantageously be selected from halogenated substituents, such as perfluorinated chains, or nitrosubstituents.

When substituents $R_1$, $R_2$, $R_3$ and $R_4$ are phenyl groups, if the phenyls are substituted, the substituents preferably occupy 2, 4 and 6 positions. Some of the preferred substituents on the phenyl groups, according to the present invention, are one Cl in position 4 or two Cl respectively in positions 4 and 6, or two methyl groups respectively in positions 2 and 6, or three methyl groups respectively in positions 2, 4 and 6 or one methoxy group in position 4, or two methoxy groups respectively in positions 4 and 6, or two trifluoromethyl groups respectively in positions 2 and 5, or two nitro groups respectively in positions 2 and 6, or fluorenyl substituents. The most preferred substituted phenyl groups have two methyl groups respectively in positions 2 and 6, or three methyl groups respectively in positions 2, 4 and 6 or one methoxy group in position 4 or two methoxy groups respectively in positions 4 and 6.

When substituents $R_1$, $R_2$, $R_3$ and $R_4$ are fluorenyl groups, if the fluorenyls are substituted, the substituents preferably occupy positions 2 and 7 or 3 and 6. The substituents if present are preferably independently selected from alkyl groups having from 1 to 6 carbon atoms, more preferably they are the same and they are t-butyl.

The ligand is prepared in two steps:

Step 1: condensation of the suitable diamine with ketone or aldehyde as described in literature for example in Reetz et al. (J. Am. Chem. Soc. 2000, 122, 996).

Step 2: reduction of the imine functions with a well-known reducing agent such as LiAlH4, NaBH4, hydrogen with Raney Nickel or Palladium on coal. The preferred reducing agent is LiAlH4.

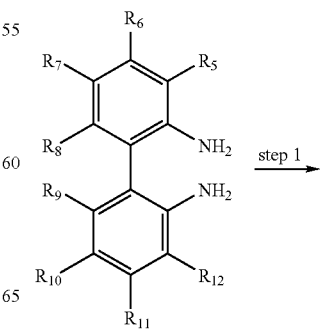

step 1

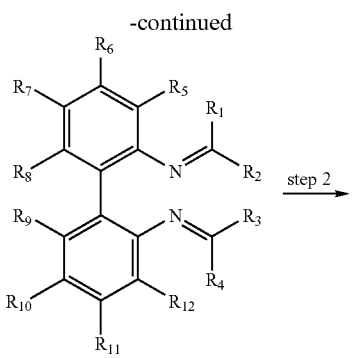

step 2

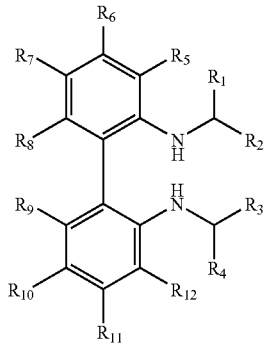

The ligand I is optionally deprotonated to form ligand I' by removing the two hydrogen atoms with a well-known base, more preferably with butyl lithium, prior to forming a metallic complex by addition of a metallic precursor.

The invention also discloses a catalyst component of formula II with the deprotonated ligand I or a catalyst of formula II' with the ligand I:

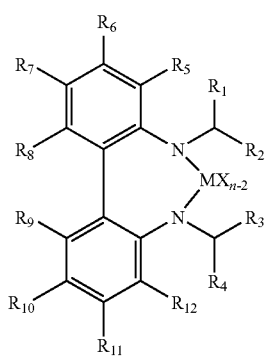
(II)

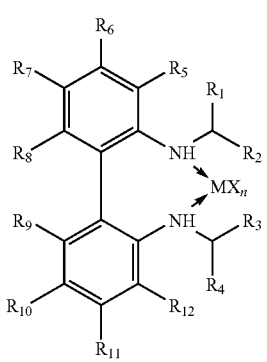
(II')

that is the condensation reaction product of the ligand of formula I or of formula I' and a metallic salt of formula $MX_n$ in a solvent, wherein M is a metal Group 3 to 10 of the periodic Table, X is the same or different and can be an organic or inorganic monovalent ligand, preferably a halogen, alcoholate, carboxylate or substituted or unsubstituted hydrocarbyl and n is the valence of M.

Preferably, M is Ti, Zr, V, Cr, Fe, Co, Ni or rare earths. More preferably, it is Ti, Zr or Cr.

Preferably X is selected from halogen, alcoholate or carboxylate. More preferably all Xs are the same and are halogen.

The solvent may be selected from dichloromethane or tetrahydrofuran and the condensation reaction is carried out at room temperature or at reflux.

The present invention also discloses an active catalyst system comprising the single site catalyst component of formula II and an activating agent having an ionising action.

Suitable activating agents are well known in the art. The activating agent can be an aluminium alkyl represented by formula $AlR^+{}_n X_{3-n}$ wherein $R^+$ is an alkyl having from 1 to 20 carbon atoms and X is a halogen. The preferred alkylating agents are triisobutyl aluminium (TIBAL) or triethyl aluminium (TEAL).

Alternatively, it can be aluminoxane and comprise oligomeric linear and/or cyclic alkyl aluminoxanes represented by formula

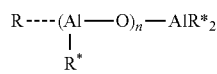

for oligomeric, linear aluminoxanes and by formula

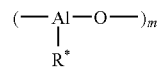

for oligomeric, cyclic aluminoxane,
wherein n is 1-40, preferably 1-20, m is 3-40, preferably 3-20 and R* is a $C_1$-$C_8$ alkyl group and preferably methyl or isobutyl.

Preferably, the activating agent is methylaluminoxane (MAO) or tetra-isobutyldialuminoxane (IBAO), more preferably, it is IBAO for Cr catalysts and MAO for Ti and Zr catalysts.

The amount of activating agent is selected to give an AVM ratio of from 100 to 3000, preferably of from 500 to 2000. The amount of activating agent depends upon its nature: for IBAO the preferred Al/M ratio is of about 500, and for MAO, it is about 2000.

Suitable boron-containing activating agents may comprise a triphenylcarbenium boronate such as tetrakis-pentafluorophenyl-borato-triphenylcarbenium as described in EP-A-0427696, or those of the general formula $[L'-H]+[B\ Ar_1\ Ar_2\ X_3\ X_4]-$ as described in EP-A-0277004 (page 6, line 30 to page 7, line 7). The amount of boron-containing activating agent is selected to give B/M ratio of from 0.5 to 5, preferably of about 1.

In another embodiment, according to the present invention, the single site catalyst component of formula II may be deposited on a conventional support. Preferably, the conventional support is silica impregnated with MAO. Alternatively and preferably, it can be an activating support such as fluorinated alumina silica.

The present invention further discloses a method for preparing an active catalyst system that comprises the steps of:
a) optionally deprotonating the ligand of formula I by removing the two hydrogen atoms;
b) complexing ligand I or deprotonated ligand I' with a metallic salt $MX_n$;
c) retrieving a catalyst component of formula II with deprotonated ligand I or II' with ligand I;
d) activating with an activating agent having an ionising action;
e) optionally adding a scavenger and/or a transfer agent;
f) retrieving an active oligomerisation or polymerisation catalyst system.

Alternatively, in step d) catalyst component II or II' is deposited on a support impregnated with an activating agent or on an fluorinated activating support.

The scavenger or transfer agent may be selected from triethylaluminium, triisobutylaluminum, tris-n-octylaluminium, tetraisobutyldialuminoxane or diethyl zinc.

The active catalyst system is used in the oligomerisation and in the polymerisation of ethylene and alpha-olefins.

The present invention discloses a method for the oligomerisation or the homo- or co-polymerisation of ethylene and alpha-olefins that comprises the steps of:
a) injecting the active catalyst system into the reactor;
b) injecting the monomer and optional comonomer either before or after or simultaneously with step a);
c) maintaining under polymerisation conditions;
d) retrieving the oligomers and/or polymer.

The pressure in the reactor can vary from 0.5 to 50 bars, preferably from 5 to 25 bars.

The polymerisation temperature can range from 10 to 100° C., preferably from 50 to 85° C.

Preferably the monomer and optional comonomer are selected from ethylene, propylene or 1-hexene.

In another preferred embodiment according to the present invention, the optional comonomer is a polar functionalised alpha-olefin.

The present invention also discloses homo- or co-polymers of ethylene obtained by polymerising ethylene with an active catalyst system described herabove.

EXAMPLES

All reactions were performed using standard Schlenk techniques or in an argon-filled glove-box. The starting materials and reagents, purchased from commercial suppliers, were used without purification. All solvents were dried and distilled before use over sodium and benzophenone for toluene, pentane, n-heptane and THF and over $CaH_2$ for dichloromethane and methanol. $^1H$ and $^{13}C$ NMR spectra were recorded on a Bruker AC300 apparatus.
Preparation of Ligands.
Synthesis of Imines.

3 mmol of bisnaphthyldiamine and 6 mmol of ketone were dissolved in 30 mL of anhydrous toluene. A few mg of para toluene sulfonic acid were added. After addition of 30 g of activated 4 angstrom molecular sieves by 10 g portions, the reaction mixture was stirred at a temperature of 110° C. for a period of time of 3 days. Molecular sieves were filtered off and the solvent was removed under vacuum. The resulting solid was crystallised from methanol to give the product. Two compounds were obtained and characterised.

Bis-naphtyldi(phenylmethyleneimine) was obtained as a yellow solid with a yield of 79%.

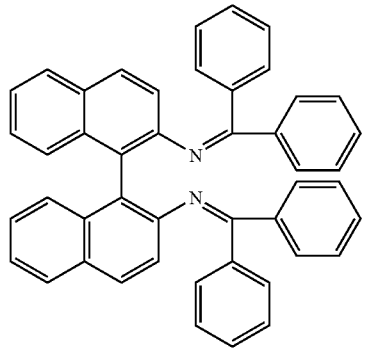 [SMILES: c1ccc(C(=Nc2ccc3ccccc3c2-c2c(N=C(c3ccccc3)c3ccccc3)ccc3ccccc23)c2ccccc2)cc1]

The NMR results were as follows.
$^1$H-RMN (300 MHz, $CD_2Cl_2$) δ (ppm): 6.64 (d, 2H), 6.74-6.78 (m, 8H), 6.93-6.97 (m, 4H), 7.05 (t, 2H), 7.19-7.48 (m, 6H), 7.50 (t, 2H), 7.68 (d, 6H), 7.77 (d, 2H)
$^{13}$C-RMN (75 MHz, $CD_2Cl_2$) δ (ppm): 122.2, 124.1, 124.2, 126.1, 126.5, 127.8, 127.9, 128.0, 128.2, 128.3, 128.9, 130.0, 130.2, 130.6, 130.7, 133.9, 136.6, 140.8, 147.6, 167.2

Bis-naphtyldi(9-fluorenylimine) was obtained as an orange solid with a yield of 69%.

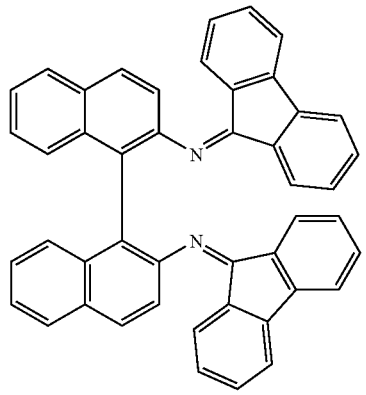 [SMILES: c1ccc2c(c1)C(=Nc1ccc3ccccc3c1-c1c(N=C3c4ccccc4-c4ccccc43)ccc3ccccc13)c1ccccc1-2]

The NMR results were as follows.
$^1$H-RMN (300 MHz, $CD_2Cl_2$) δ (ppm): 6.0 (m, 4H), 6.41 (d, 4H), 6.73 (t, 8H), 7.0-7.50 (m, 24H), 7.85 (d, 4H), 7.94 (d, 4H).
$^{13}$C-RMN (75 MHz, $CD_2Cl_2$) δ (ppm): 119.7, 119.8, 120.9, 123.4, 124.4, 125.2, 125.8, 126.4, 126.9, 127.2, 127.5, 128.1, 128.5, 128.7, 129.1, 129.5, 131.5, 131.6, 131.9, 133.6, 138.2, 142.2, 143.4, 149.0, 163.3.
Synthesis of Amines.

0.9 mmol of Bis-naphtyldi(phenylmethyleneimine) or Bis-naphtyldi(9-fluorenylimine) were dissolved in 150 mL of anhydrous THF. 8 equivalents of $LiAlH_4$ were added and the reaction mixture was stirred overnight under reflux. During the reaction, 12 equivalents of $LiAlH_4$ were added at a rate of 8 equivalents at t=4 hours and 4 equivalents at t=20 hours. After one night the solution was cooled at room temperature and 500 μL of water were slowly added. After addition of 500 μL of aqueous solution of NaOH 15% and 1500 μL of water, the mixture was filtered off and the solvent was removed in vacuum. Two compounds were obtained and characterised.
Bis-naphtyldi(phenylmethyleneamine) (L1)
Ligand L1 was obtained as a beige solid with a yield of 86%.

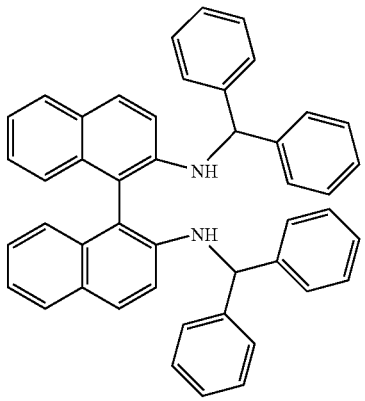

L1

The NMR results were as follows.
¹H-RMN (300 MHz, CDCl₃) δ (ppm): 4.49 (d, 2H), 5.73 (d, 2H), 7.08 (m, 8H), 7.16 (m, 7H), 7.23 (m, 13H), 7.73 (m, 4H).

Bis-naphtyldi(9-fluorenylamine) (L2)
Ligand L2 was obtained as a pale yellow solid with a yield of 80%.

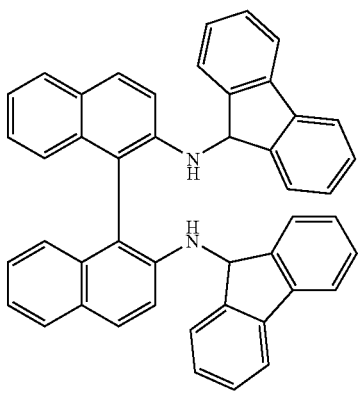

L2

The NMR results were as follows:
¹H-RMN (300 MHz, CD₂Cl₂) δ (ppm): 4.51 (d, 2H), 5.62 (d, 2H), 7.06 (m, 6H), 7.25 (m, 8H), 7.38 (dt, 4H), 7,49 (d, 2H), 7.74 (m, 8H).
¹³C-RMN (75 MHz, CD₂Cl₂) δ(ppm): 59.4, 112.4, 114.9, 119.9, 120.1, 122.1, 123.8, 124.4, 126.7, 127.4, 127.5, 127.9, 128.0, 128.2, 128.3, 129.5, 133.8, 139.9, 140.0, 143.8, 145.2, 145.6.

Preparation of Complexes.
Synthesis of Ti(IV) Complexes A.
115 mg (0.2 mmol) of ligand L1 were dissolved in 5 mL of THF and cooled to a temperature of −78° C. 0.4 mmol of n-butyl lithium (C=1.6M in hexane) were added dropwise. The brown solution was stirred for 2 hours at room temperature. 0.2 mL (0.2 mmol) of TiCl₄ (C=1M in toluene) were dissolved in 5 mL of THF and cooled to a temperature of −78° C. The solution of anionic ligand was added dropwise to the solution of TiCl₄, and it was stirred at room temperature overnight. The mixture was evaporated to dryness and the complex was extracted with 10 mL of dry dichloromethane. The filtrate was concentrated to approximately 2 mL, and 10 mL of pentane were added. Solvents were filtered off and the solid was washed twice with pentane. The resulting solid was dried under vacuum to afford 115 mg of complex A1 as a yellow brown powder with a yield of 84%.

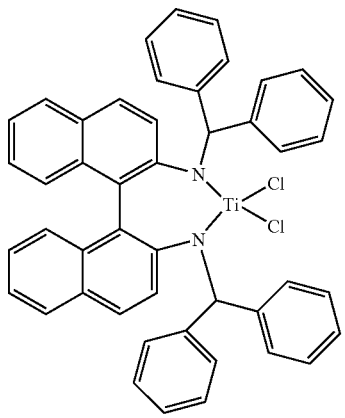

A1

Similarly, Ti(IV) complex A2 was obtained from ligand L2 to afford a brown solid with a yield of 73%.

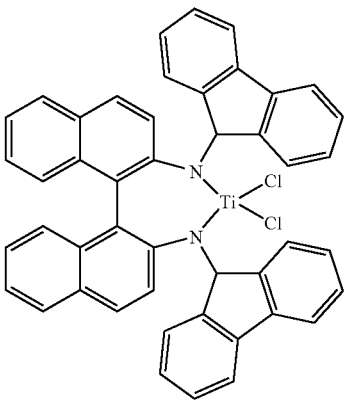

A2

Synthesis of Zr(IV) Complex B1.
110 mg (0.2 mmol) of ligand L1 were dissolved in 5 mL of THF and cooled to a temperature of −78° C. 0.4 mmol of n-butyl lithium (C=1.6 M in hexane) were added drop-wise. The brown solution was stirred for 30 minutes at room temperature. 0.2 mmol of ZrCl₄ were dissolved in 5 mL of THF and cooled to a temperature of −78° C. The solution of the anionic ligand was added drop-wise to the solution of ZrCl₄. The resulting solution was stirred overnight under reflux at a temperature of 70° C. The mixture was evaporated to dryness and the complex was extracted with 10 mL of dry dichloromethane. The filtrate was concentrated to approximately 2 mL, and 10 mL of pentane were added. Solvents were filtered off and the solid was washed twice with pentane. The resulting solid was dried under vacuum to afford 115 mg of complex B1 as a yellow powder with a yield of 84%.

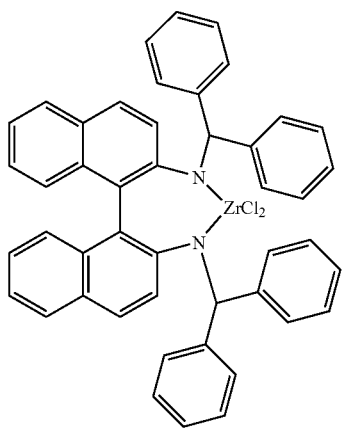

B1

Synthesis of Cr(III) Complexes C.

Cr(III) Complexes Obtained from Neutral Ligands 102 mg (0.2 mmol) of ligand L1 were dissolved in 5 mL of THF and added to a solution of 64 mg (0.2 mmol) of CrCl₃.3THF in 5 mL of THF. The solution was stirred at room temperature overnight. The mixture was concentrated to approximately 2 mL and 10 mL of pentane were then added. Solvents were filtered off and the solid was washed twice with pentane. The resulting solid was dried under vacuum to afford 128 mg of complex C1a as a pink powder with a yield of 75%.

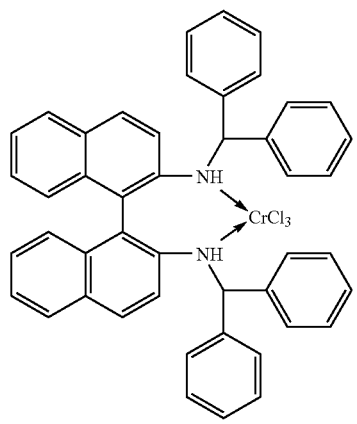

C1a

Similarly, Cr(III) complex C2a was obtained from ligand L2 to afford a pale brown solid with a yield of 98%

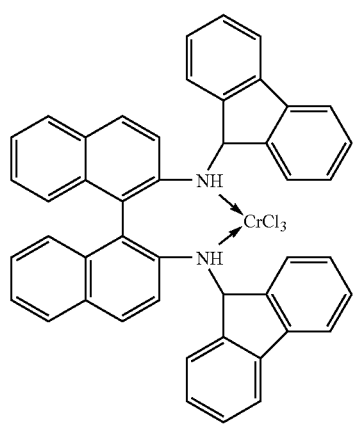

C2a

Cr(III) Complexes Obtained from Di-Anionic Ligands 120 mg (0.2 mmol) of ligand L2 were dissolved in 5 mL of THF and cooled to a temperature of −15° C. Two equivalents of n-butyl lithium (C=1.6M in hexane) were added dropwise. The solution was stirred for 30 minutes and added to a solution of 76 mg (0.2 mmol) of CrCl₃.3THF dissolved in 5 mL of THF. The solution was stirred at room temperature overnight. The mixture was concentrated to approximately 2 mL and 10 mL of pentane were then added. Solvents were filtered off and the solid was washed twice with pentane. The resulting solid was dried under vacuum to afford 130 mg of complex C2b as a green powder with a yield of 95%.

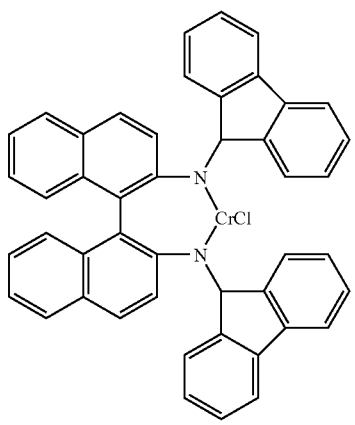

C2b

Similarly, Cr(III) complex C1b was obtained from ligand L1 to afford a pale green solid with a yield of 42%

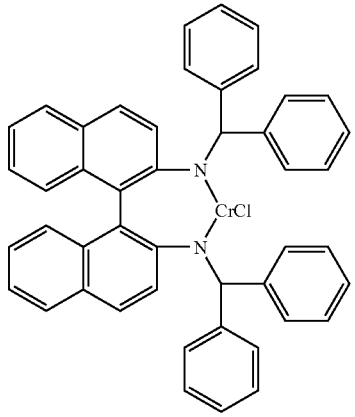

C1b

Synthesis of Fe(II) Complexes D.

100 mg (0.2 mmol) of ligand L1 were dissolved in 5 mL of THF. 33 mg (0.2 mmol) of FeCl₂.4H₂O were dried under vacuum during one hour at a temperature of 120° C. The solution of ligand was added to the solution of FeCl₂ in 5 mL of THF. The solution was stirred at room temperature overnight. The mixture was concentrated to approximately 2 mL and 10 mL of pentane were then added. Solvents were filtered off and the solid was washed twice with pentane. The resulting solid was dried under vacuum to afford 86 mg of complex D1 as a grey powder with a yield of 72%.

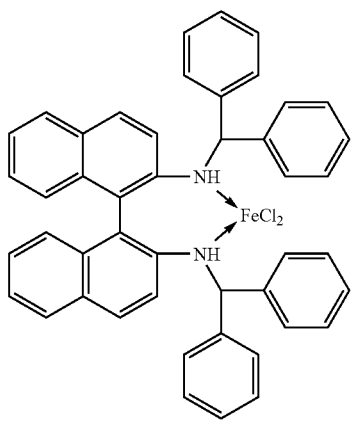

D1

Similarly, Fe(II) complex D2 was obtained from ligand L2 to afford a brown solid with a yield of 83%

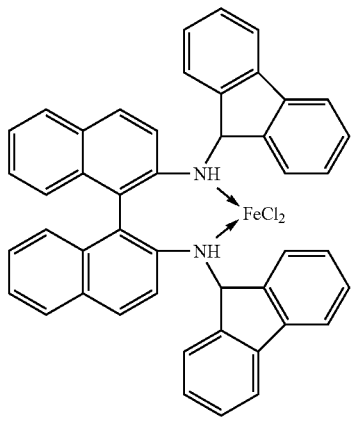

D2

Synthesis of Fe(III) Complexes E.
Fe(III) Complexes Obtained from Neutral Ligands 120 mg (0.2 mmol) of ligand L2 were dissolved in 5 mL of THF and added to a solution of 33 mg (0.2 mmol) of FeCl₃ in 5 mL of THF. The solution was stirred at room temperature overnight. The mixture was concentrated to approximately 2 mL and 10 mL of pentane were then added. Solvents were filtered off and the solid was washed twice with pentane. The resulting solid was dried under vacuum to afford 140 mg of complex E2a as a brown powder with a yield of 93%.

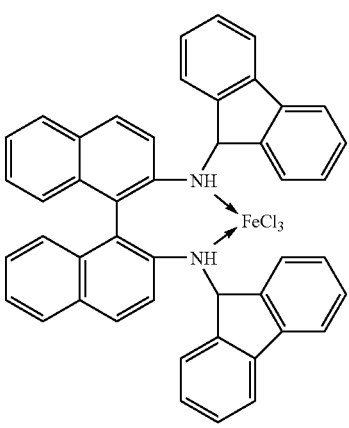

E2a

Fe(III) Complexes Obtained from Di-Anionic Ligands 99 mg (0.2 mmol) of ligand L2 were dissolved in 5 mL of THF and cooled to a temperature of −15° C. Two equivalents of n-butyl lithium (C=1.6M in hexane) were added dropwise. The brown solution was stirred for 30 minutes at room temperature. 27 mg (0.2 mmol) of FeCl₃ were dissolved in 5 mL of THF and cooled to a temperature of −15° C. The solution of anionic ligand was added dropwise to the solution of FeCl₃ and it was stirred at room temperature overnight. The mixture was concentrated to approximately 2 mL and 10 mL of pentane were then added. Solvents were filtered off and the solid was washed twice with pentane. The resulting solid was dried under vacuum to afford 92 mg of complex E2b as a pale orange powder with a yield of 81%.

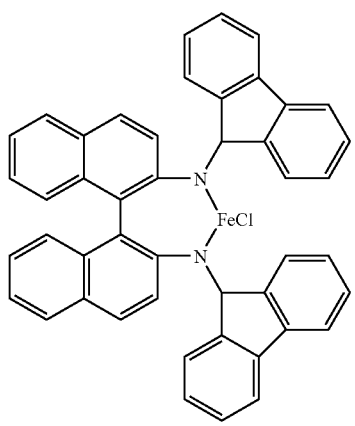

E2b

Synthesis of Ni(II) Complexes F.

104 mg (0.2 mmol) of ligand L1 were dissolved in 5 mL of CH₂Cl₂ and added to a solution of 54 mg (0.2 mmol) of Nickel(II) bromide ethylene glycol dimethyl ether complex in 5 mL of CH₂Cl₂. The solution was stirred at room temperature overnight. The mixture was evaporated to dryness and the complex was extracted with 10 mL of dry dichloromethane. The filtrate was concentrated to approximately 2 mL, and 10 mL of pentane were added. Solvents were filtered off and the solid was washed twice with pentane. The resulting solid was dried under vacuum to afford 43 mg of complex F1 as a pale yellow powder with a yield of 31%.

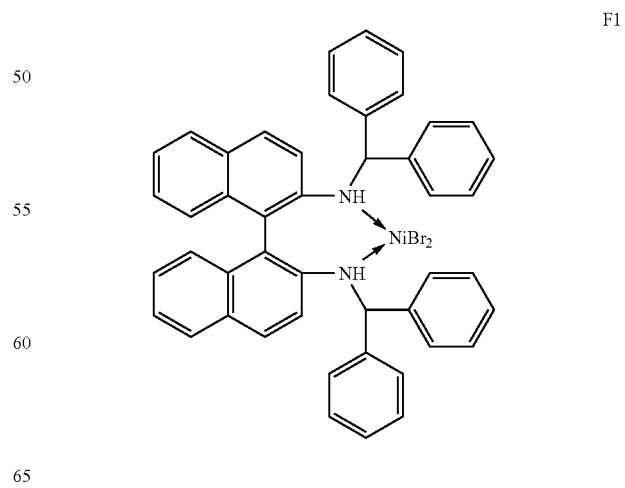

F1

Similarly, Ni(II) complex F2 was obtained from ligand L2 to afford a yellow solid with a yield of 56%.

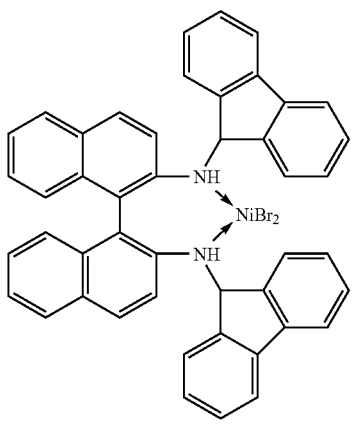

F2

Polymerisation of Ethylene with MAO as Activating Agent.

Ethylene polymerisation reactions were carried out in a 20 mL stainless steel autoclave containing a glass insert, fitted with mechanical stirring, external thermocouple and pressure gauge and controlled by a computer. In a typical reaction run, the temperature was set to the desired value (50 or 80° C.) and 4 mL of dry solvent (toluene or n-heptane) were introduced into the reactor under nitrogen flow. In an argon-filled glove box, about 4 mg (5 µmol) of the appropriate catalyst were weighted, activated with methylaluminoxane (MAO) (30% wt in toluene) in an appropriate amount to obtain a ratio [Al]:[M] of 2000, and the resulting active complex was diluted with toluene to obtain a final volume of 2 mL. 200 µL of the solution of activated catalyst were placed inside the reactor. The injection loop was rinsed with 800 µL of solvent. The ethylene pressure was raised to the desired value (15 bar at 50° C. and 19 bar at 80° C.) and continuously fed into the reactor. After either 1 hour or an ethylene consumption of 12 mmol, the reactor was cooled down and depressurised, then the reaction was quenched with isopropanol and the solution was analysed by gas chromatography, to determine if oligomers were formed. The gas chromatographic (GC) analysis of the reaction products was performed on a Trace GC apparatus with a Petrocol capillary column (methyl silicone, 100 m long with i.d. of 0.25 mm and film thickness of 0.5 µm) working at a temperature of 35° C. for 15 min and then heating at a rate of 5° per minute up to a temperature of 250° C. The results for the polymerisation of ethylene with MAO are displayed in Table 1 for polymerisation with catalyst systems based on metal group 4 of the Periodic Table (A and B) and in Table 2 for oligomerisation with Cr(III) catalysts (C).

The Iron and Nickel complexes were inactive towards ethylene polymerisation.

TABLE 1

| | | | Activity | DSC | |
|---|---|---|---|---|---|
| Run | Complex | m PE (mg) | (kg/mol/h) | Tm (° C.) | ΔH (J·g$^{-1}$) |
| 1 | A1 | 235 | 466 | 134.2 | 107.4 |
| 2 | A2 | 243 | 479 | 135.6 | 121.9 |
| 3 | B1 | 153 | 305 | 135.1 | 134.4 |

All Reactions were performed with 0.5 µmol of catalyst dissolved in 5 mL of n-heptane, at a temperature of 80° C. and with an ethylene pressure of 19 bars, running for 60 minutes. The amount of activating agent (MAO) was adjusted to yield a ratio. [Al]:[M] of 2000. Activities are expressed in kg of polyethylene per mol of metal per hour.

$^{13}$C NMR analysis did not show any branching for the samples studied.

TABLE 2

| | | | | % C4 | | % C6 | | % C8-C22 |
|---|---|---|---|---|---|---|---|---|
| Run | Complex | m PE (mg) | Activity (kg/mol/h) | Total | α-C4 | Total | α-C6 | |
| 4 | C1a | 12 | 1449 | 19 | >99.5 | 26 | 98 | 55 |
| 5 | C1a | 26 | 197 | 13 | >99.5 | 18 | 87 | 59 |
| 6 | C2a | 13 | 1780 | 18 | 96 | 25 | 95 | 57 |
| 7 | C2a | 53 | 222 | 13 | >99.5 | 24 | 90 | 63 |
| 8 | C2b | 38 | 106 | not analysed | | | | |

All Reactions were performed with 0.5 µmol of catalyst dissolved in 5 mL of solvent, at a temperature of 50° C. and with an ethylene pressure of 15 bars. The amount of activating agent (MAO) was adjusted to yield a ratio [Al]:[M] of 2000. Runs 4 and 6 were performed in toluene, whereas runs 5, 7 and 8 were performed in n-heptane.

Reaction times were of 60 minutes for runs 5, 7 and 8, of 28 minutes for run 4 and of 22 minutes for run 6.

Mixtures of polyethylene and oligomers were obtained. Oligomers were characterised by gas chromatography. Activities are expressed in kg of ethylene consumed per mol of Cr per hour.

Polymerisation of Ethylene with IBAO as Activating Agent.

The procedure was the same as that described above with MAO except that the catalyst was activated with appropriate amounts of tetraisobutyldialuminoxane (IBAO, 10% wt in toluene). The polymerisation results are displayed in Table 3.

TABLE 3

| | | | Activity | DSC | |
|---|---|---|---|---|---|
| Run | Complex | m PE (mg) | (kg/mol/h) | Tm (° C.) | ΔH (J·g$^{-1}$) |
| 9 | C1a | 110 | 219 | 137.6 | 89.0 |
| 10 | C2a | 237 | 469 | 136.2 | 134.6 |

All reactions were performed with 0.5 µmol of catalyst dissolved in 5 mL of n-heptane, at a temperature 50° C. under an ethylene pressure of 15 bars and with IBAO as activating agent, running for 60 minutes. The amount of activating agent IBAO was adjusted to yield a ratio [Al]:[Cr] of 500. Activities are expressed in kg of polyethylene per mol of Cr per hour.

$^{13}$C NMR analysis did not show any branching for these two samples.

The invention claimed is:

1. An active catalyst system comprising:
a catalyst component of formula II or of formula II'

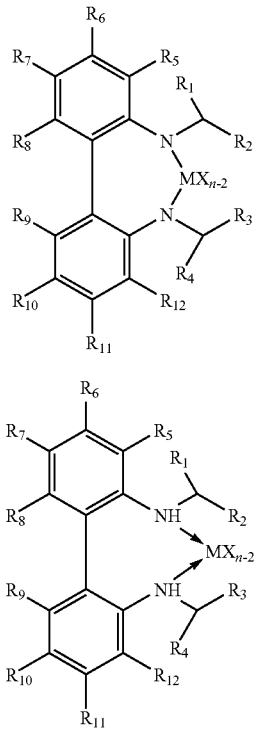

obtained by condensation reacting of a metallic salt $MX_n$ and a bidentate ligand of formula I

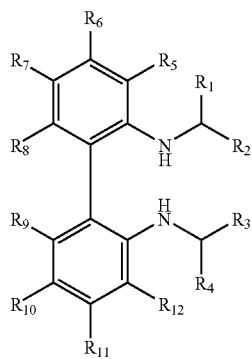

wherein $R_1$, $R_2$, $R_3$, $R_4$ are each independently selected from the group consisting of unsubstituted or substituted alkyl groups, unsubstituted or substituted aryl groups, and unsubstituted or substituted cycloalkyl groups;

wherein $R_5$, $R_6$, $R_7$, $R_8$, $R_9$, $R_{10}$, $R_{11}$ and $R_{12}$ are each independently selected from the group consisting of hydrogen, unsubstituted or substituted hydrocarbyls and inert functional groups, and wherein two or more R's can be linked together to form further ring or rings;

wherein M is a metal Group 3 to 10 of the periodic Table, each X is the same or different and is selected from halogens, alcoholates, carboxylates and substituted or unsubstituted hydrocarbyls and n is the valence of M; and an activating agent having an ionising action.

2. The active catalyst system of claim 1, wherein $R_1$, $R_2$, $R_3$ and $R_4$ are the same and are Ph, wherein Ph is phenyl or wherein $R_1$ and $R_2$ on one hand and $R_3$ and $R_4$ on the other hand are linked together and form fluorenyl groups.

3. The active catalyst system of claim 2, wherein $R_1$, $R_2$ $R_3$ and $R_4$ are substituted with halogenated chains.

4. The active catalyst system of claim 2, wherein the phenyl groups or the fluorenyl groups are unsubstituted.

5. The active catalyst system of claim 1, wherein $R_5$, $R_6$, $R_7$, $R_8$, $R_9$, $R_{10}$, $R_{11}$ and $R_{12}$ are each independently selected from the group consisting of hydrogen, alkyl groups, aryl groups and cycloalkyl groups.

6. The active catalyst system of claim 5, wherein $R_5$, $R_6$, $R_{11}$ and $R_{12}$ are the same and are hydrogen, and wherein $R_7$ and $R_8$ together, as well as $R_9$ and $R_{10}$ together, are joined to form unsubstituted naphthyl groups.

7. The active catalyst system of claim 1, wherein each X is the same and is halogen.

8. The active catalyst system of claim 1, wherein the activating agent is methylaluminoxane or tetraisobutyldialuminoxane.

9. A method for preparing the active catalyst system of claim 1 comprising:
optionally removing two hydrogen atoms from the ligand I in order to prepare deprotonated ligand I';
complexing ligand I or deprotonated ligand I' with metallic precursor $MX_n$;
adding an activating agent having an ionising action;
optionally adding a scavenger, transfer agent or combinations thereof; and
retrieving the active catalyst system.

10. A method for oligomerising or homo- or co-polymerisisng ethylene or alpha-olefins comprising:
injecting the active catalyst system of claim 1 into a polymerization reactor;
injecting monomer and optional comonomer into the polymerization reactor;
maintaining the polymerization reactor under polymerisation conditions to form oligomers, polymers or combinations thereof; and
retrieving the oligomers, polymers or combinations thereof.

11. The method of claim 10, wherein the monomer and optional comonomer are selected from ethylene, propylene, 1-hexene or combinations thereof.

* * * * *